United States Patent [19]

Richard

[11] Patent Number: 4,516,583

[45] Date of Patent: May 14, 1985

[54] ULTRASONIC ECHOGRAM PROBE AND SECTOR ECHOGRAPHIC SCANNING DEVICE

[75] Inventor: Bruno Richard, Brunoy, France

[73] Assignee: Centre National de la Recherche Scientifique, Paris, France

[21] Appl. No.: 396,078

[22] Filed: Jul. 7, 1982

[30] Foreign Application Priority Data

Jul. 8, 1981 [FR] France ............................... 81 13445

[51] Int. Cl.[3] .............................................. A61B 10/00

[52] U.S. Cl. ....................................... 128/660; 73/626

[58] Field of Search ................................ 128/660-661; 73/625-626

[56] References Cited

U.S. PATENT DOCUMENTS

| | | | |
|---|---|---|---|
| 4,208,916 | 6/1980 | Thomenius et al. | 128/660 X |
| 4,253,338 | 3/1981 | Iinuma et al. | 128/660 X |
| 4,319,489 | 3/1982 | Yamaguchi et al. | 128/660 X |
| 4,344,327 | 8/1982 | Yoshikawa et al. | 128/661 X |
| 4,372,323 | 2/1983 | Takemura et al. | 128/660 |
| 4,409,982 | 10/1983 | Plesset et al. | 128/660 |

*Primary Examiner*—Kyle L. Howell
*Assistant Examiner*—Francis J. Jaworski
*Attorney, Agent, or Firm*—Larson and Taylor

[57] ABSTRACT

The device, particularly useful for B echographic examination of an organ or of an internal anatomical structure, comprises a line array of N identical transducer elements ($12_i, \ldots, 12_N$) distributed at equal intervals and operating at a predetermined frequency f, means for storing at least one distribution of delays of n successive transducers (n being less than N) corresponding to focussing at a predetermined distance from the line for frequency f, switch means enabling a group of n transducers to be connected temporarily to signal emitting or receiving means with delays corresponding to the distribution and the group of n transducers to be shifted so as to effect scanning. The transducers are arranged along a circular line with the convex side turned toward said medium so as to cause sector scanning around the axis of the circular line on operation of switch commutator means and the time delays are arranged to ensure focussing along the radius corresponding to the middle transducer of the group.

6 Claims, 5 Drawing Figures

FIG.1.
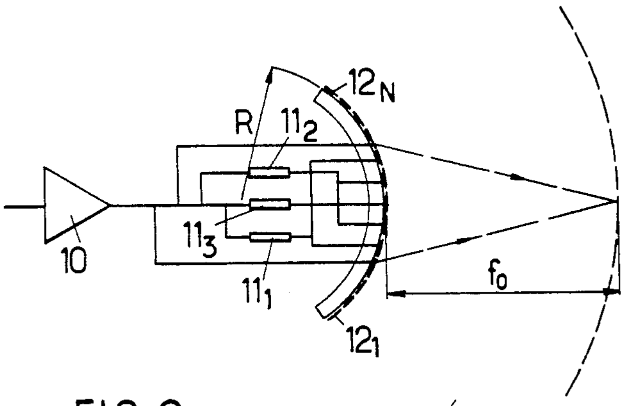
FIG.2.
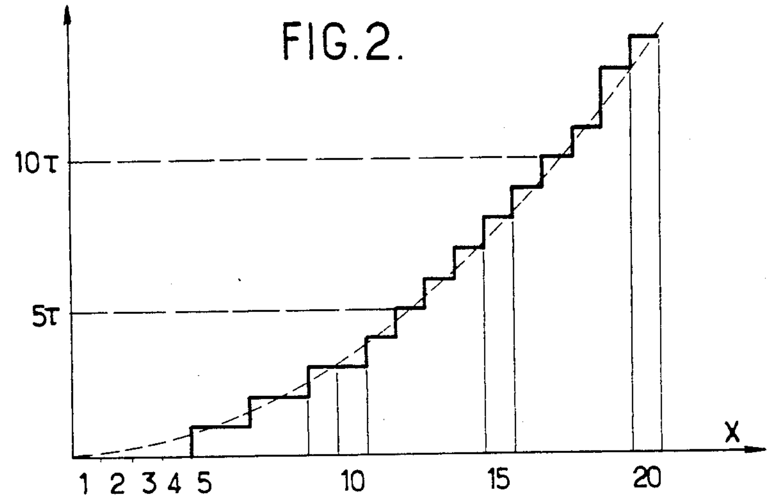
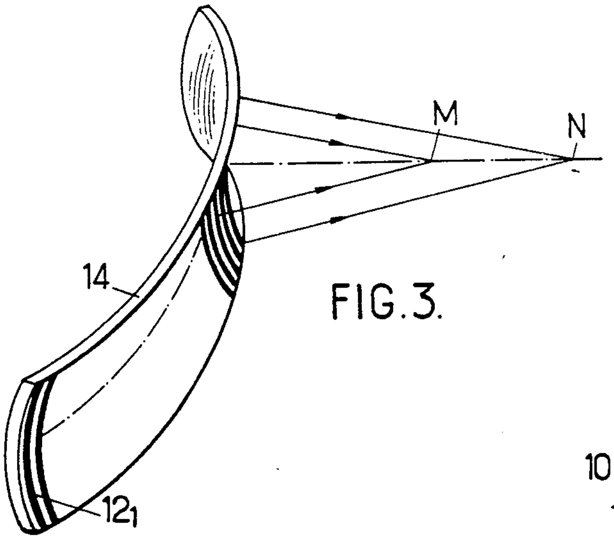
FIG.3.
FIG.4.
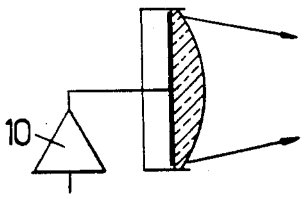

ULTRASONIC ECHOGRAM PROBE AND SECTOR ECHOGRAPHIC SCANNING DEVICE

FIELD OF THE INVENTION

The present invention relates to an ultrasonic pulse echography probe and to a device using such a probe. The invention has a particularly important application in the medical field.

PRIOR ART

Very many ultrasonic echographic devices are already known which enable exploration of an organ or of an internal anatomical structure. Among these devices, many ensure focusing at a predetermined depth, corresponding to an area to be examined, on transmission and/or on reception. This focusing is provided electronically or optically. In the first case, delay lines or phase shift elements (certificate of addition No. FR 2.335.288). are generally used. In this way, by only using several elements providing discrete phase shifts or delays, a distribution is approached which would corespond to strict focusing.

The exploration in depth of an organ or of an anatomical structure (B echography) frequently involves scanning. Ultrasonic echography devices have already been produced which ensure both focusing and line or sector scanning. In the case of medical uses, sector scanning has the great advantage of permitting exploration of internal anatomical structures from a very small contact surface with the skin. It enables particularly the display of the operation of the cardiac muscle by means of a probe placed so that the ultrasonic beam passes between two successive ribs.

The scanning can be carried out electronically or mechanically. In particular, fully satisfactory devices with line scanning are known, using a small bar including a number N of transducer elements (see the certificate of addition already mentioned). The scanning is carried out by moving on each shot the group n of transducers used simultaneously with a distribution of delays or of phases ensuring the focusing at the required distance. On the other hand, angular scanning by modification of the distribution of the phases applied to a group of transducers used for all directions (U.S. Pat. No. 4.070,905) leads to very complicated and expensive electronic technology. As for the devices with mechanical sector scanning, using a rotary exploration head, they have the drawback of being generally less reliable mechanically than purely electronic devices with a fixed scan head.

An attempt has been made to produce devices ensuring at the same time focusing and sector scanning by means of a probe comprising a row of N adjacent transducer elements positioned at regular intervals over a cylindrical area whose concavity is directed towards the organ under examination. The group of N transducers used are shifted simultaneously, from one shot to the next, to cause the scanning around an axis which corresponds substantially to the contact point with the skin in the case of a medical apparatus.

This solution has various drawbacks. It leads to a bulky and complex probe and lends itself poorly to focusing electronically.

It is an object of the present invention to provide an ultrasonic echography device which permits a sector scan to be carried out simply and naturally, associated with focusing which can be easily produced at a variable distance, that is to say, focusing of the type currently referred to as "tracking focusing".

The device comprises a probe having a support surface designed to be placed in contact with the organ to be examined, bearing a linear array of N identical transducer elements distributed at equal intervals connected electrically to switching means for temporary connecting a group of n transducers at the same time to signal transmission or reception means with delays corresponding to a distribution providing focusing at a predetermined distance and shifting the group of n transducers from one shot to the next, so as to effect scanning, the transducers are arranged along a line whose convex side faces toward an organ to be examined whereby sector scanning occurs naturally. The arrangement represents a complete departure from prior art constructions using a curved array of transducer elements, in that in these prior constructions the concave side of the array faces toward the organ to be examined. It will be understood that, in the latter case, the arrangement of the transducers leads to almost automatic focusing. In fact, there is indeed on the contrary an obligatory divergence, due to the fact that the ultrasonic beam only penetrates into the organ to be examined beyond its focusing zone, which the geometry itself of the probe imposes a non-variance. The invention seeks also to provide an echography device enabling the use of a probe of the above type and, with very little additional equipment probes of other types such as those using a flat bar of transducers. To this end, the invention provides an ultrasonic echography device for exploring a medium and particularly an organ or internal anatomical structure, comprising a linear array of N identical transducer elements distributed at equal intervals, means for storing at least one distribution of the time delays to be associated with n successive transducers (n being less than N) corresponding to focusing at a predetermined distance from the line, switching means enabling a group of n transducers to be connected temporarily to signal transmission or reception means with delays corresponding to said distribution and the group of n transducers to be shifted so as to effect a scanning, characterized in that the transducers are arranged over a circular line with convexity turned toward said medium so as to cause a sector scan around the axis of the circular line on the operation of the switching means and in that the delays are provided to ensure focusing along the radius corresponding to the middle point of the group, at a predetermined and, if necessary, variable distance.

The delays may be ensured by delay lines or similar phase shift elements. The first solution will generally be preferable, especially to the extent that the delay means enable this delay to be varied continuously.

The probe and the device defined above have numerous advantages: they have great flexibility of operation, since they lend themselves perfectly to dynamic focusing; and due to the fact that the transducers are immediately next to the medium to be explored, the density of the exploration lines will present less variation between surface areas and deep areas than in the case of flat probes or circular probes whose concave side is turned towards the medium. Focusing by geometric or electronic means remains possible in the direction perpendicular to the plane of the line over which the transducers are spread. The electronic means of operation remain very simple, due to the fact that the angular scan is effected automatically along a sector having as a center the axis of distribution of the transducer elements. The electronic system of the device enables successive operation with very different probes, particularly as regards the radius of the circle over which the transducers are spread and the spacing of the transducers.

It can be noted in passing that submarine sounding systems are known comprising hydrophones distributed over a circle, and enabling angular exploration. However this involves a technology which is extremely different from that envisaged here, where the hydrophones are surrounded by the medium to be explored and operate under totally different conditions.

It appears in fact that the solution proposed by the invention has hitherto been avoided by the technicians skilled in the art due to the fact that apparently it goes contrary to the focusing which is sought to ensure good lateral definition, the distribution over a convex surface tending to provide or to collect the energy in a beam which increases in divergence as the transducer elements are spread over a circle of small radius. Applicant was obliged, to arrive at the invention, to take the opposite course to the established attitude by extending to such a distribution of transducer elements the focusing techniques used particularly in the case of flat bars of transducers.

This similarity of the invention to prior art focusing techniques makes it possible to use the same electronic systems, at the price of simple changes of components or of logic, with both a conventional line scan probe and a sector scan probe of the type defined above, which constitutes a distinct advantage over conventional devices. In fact, for almost the same cost, the possibilities of use of a device are practically doubled.

It is also an object of the invention to provide an ulrasonic echography device having a better signal/-noise ratio than the prior art devices, and which produces accurate focusing due to the use of fine sampling of the delays, without however increasing the price prohibitively.

GENERAL DESCRIPTION OF THE INVENTION

Accordingly, the invention provides particularly an ultrasonic echography device for exploring a medium, and especially an organ or an internal anatomical structure, characterized in that it comprises a probe having a line array of N identical transducer elements distributed at equal intervals, for pulse energization, and an electronic system comprising means for storing at least one distribution of delays over n successive transducers (n being less than N) corresponding to focusing at a predetermined distance from the line, switching means enabling one group of n transducers to be connected temporarily to signal transmission or reception means with delays corresponding to said distribution and the group of n transducers to be shifted so as to effect a scan, the delays being provided to ensure focusing at a predetermined and, if necessary, variable distance and the switching means comprising:

delay means providing, over a different channels, from the same pulse coming from the transmission means, a pulses having different delays, n first multiplexers each enabling one of the a channels to be connected temporarily to an input-output terminal of the multiplexer, and n second multiplexers each of which is inserted between the terminal of a first corresponding multiplexer and several of the N transducers which are shifted by n, each second multiplexer enabling one of the transducers to be connected to the first multiplexers during the time necessary for a transmission and for the corresponding reception.

This arrangement enables the number of first multiplexers to be limited to n, whatever the number N of the transducers of the probe, which notably reduces the cost and permits multiplexers to be adopted having a high number a of channels without however arriving at an excessive cost. It is thus easily possible to adopt a number a of channels and of delays at least equal to 16, this number enabling the quality criteria required for medical uses to be fulfilled. As for the numbers N and n, they can respectively be 160 and 40 (figures which are rarely exceeded to constitute a lens).

Each of the second multiplexers comprises advantageously a transmission element or transmitter, ensuring the direct connection between said terminal and a transducer, and a reception element, ensuring the connection through a preamplifier between the transducer and the terminal of the first multiplexer and in that said elements are activated by means synchronized with the transmission means so as to block the transmission element during the reception period and to enable the transmission element during the transmission period.

Due to this arrangement, different paths are used for transmission and reception, so that it is possible to use a preamplifier with a high gain without risk of interaction with the transmission. The signals received at low level are thus brought to a sufficient level in the preamplifiers which can be quality preamplifiers and with very low noise without excessive cost, since their number is reduced with respect to that of the transducers.

It is possible to provide in the device several sets of multiplexers and of transmission and reception elements adapted to various types of probes, as well as switching means. The latter enable the operation of one or the other of the sets according to the probe used. The switching means can be limited to an address generator causing the operation of a particular set. The switching means can also be provided to operate at will any one of several storage memories for different delay distributions.

BRIEF DESCRIPTION OF THE DRAWINGS

The invention will be better understood on reading the description which follows of particular embodiments of the invention purely by way of non-limiting example. The description refers to the accompanying drawings, wherein:

FIG. 1 shows diagrammatically the principle of the arrangement of the n transducer elements in a probe for practicing the invention, FIG. 2 is a diagram showing the distribution of delays arranged to be applied to the transducers distributed at equal angular intervals to ensure focusing at a predetermined distance;

FIG. 3 is a perspective view showing a possible constitution of the head enabling double focusing to be effected with sector scanning, FIG. 4 is a diagrammatic view in section of the head showing a second arrangement enabling focusing to be carried out in a plane perpendicular to the scanning plane.

DESCRIPTION OF PREFERRED EMBODIMENTS

Figure 5:
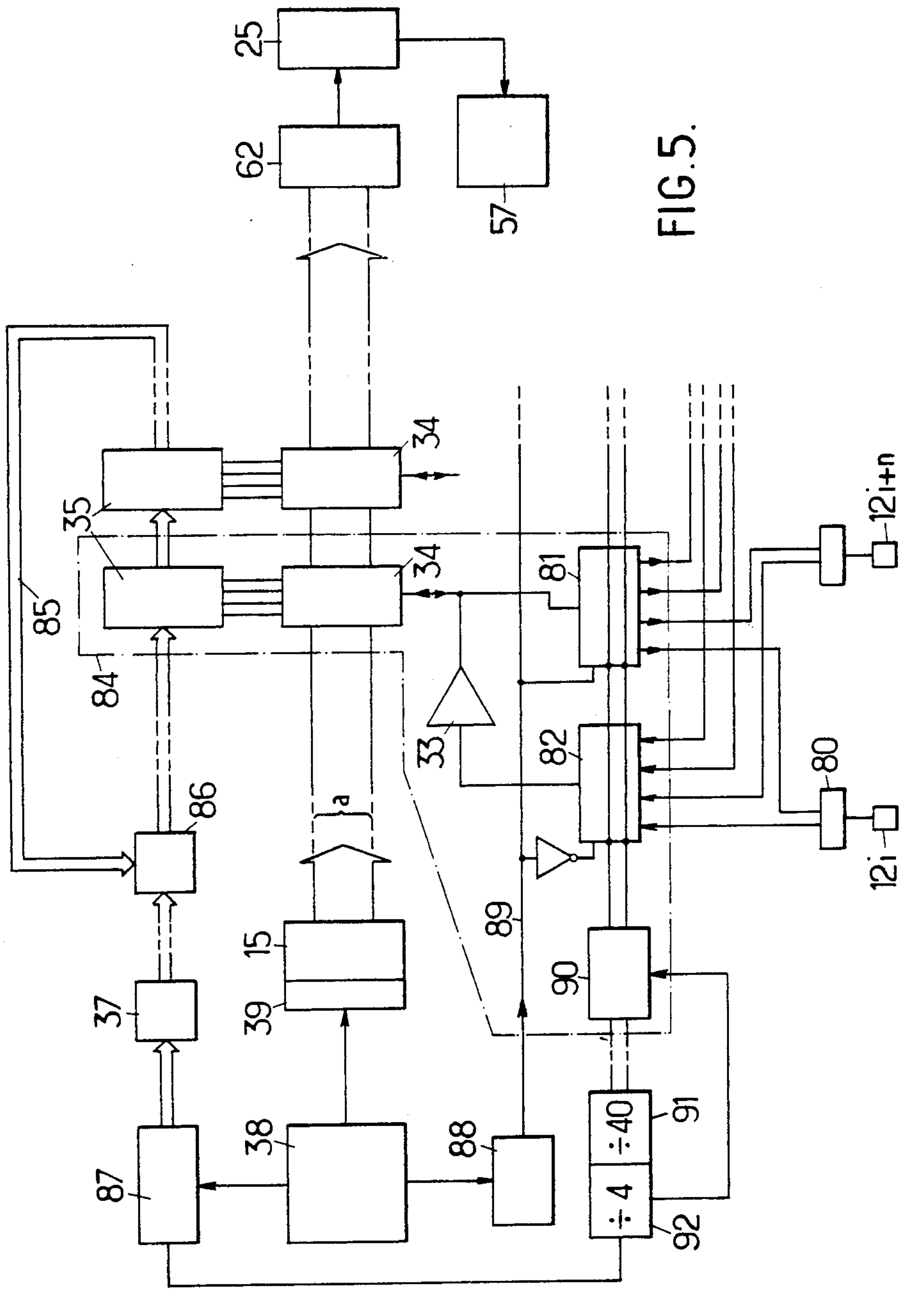
FIG. 5 is a schematic diagram of a circuit enabling carrying out of the invention, in association with a probe of the type shown in FIG. 3.

As has already been indicated in certificate of addition published as no. 2,335,288, already mentioned, and French Pat. No. 2,492,982, to which reference may be made, it is possible to carry out focusing on transmission or on reception in line with a group of n transducers distributed over a direction x'—x at a distance $f_O$ from a right angle segment on which are distributed the n elementary transducers, using a delay distribution between the transducers as a function of the abscissa x from the center O of the transducer group.

The invention necessitates the formation of a similar focus by means of a probe of the type shown in FIG. 1, comprising N transducer elements $\mathbf{12}_1, \ldots, \mathbf{12}_i, \ldots, \mathbf{12}_N$. For purposes of clarity, only twelve transducer elements have been illustrated (N=12). However, a much greater number of transducer elements (for instance N=160) will typically be used in actual embodiments. Again, for simplicity, only seven transducer elements have been represented as being energized during a particular shot. In fact that number n of transducer elements used on each shot would typically be much greater. The focusing at distance $f_O$ of the ultrasonic energy radiated by the transducers spread over a circle of radius R can be ensured by feeding the n transducers, from a common pulse source, through suitable delay units. The delays to be used are substantially the same as those necessary to focus the energy of transducers spread along a line bar at distance F, F being connected with R and with $f_O$ by the formula:

$$1/F=1/R-1/f_O.$$

In FIG. 1, there is shown diagrammatically, downstream from a pulse amplifier 10 constituting the energy emitting source, a set of three delay lines $\mathbf{11}_1$, $\mathbf{11}_2$ and $\mathbf{11}_3$ supplying increasing and suitable delays. The energization pulse is applied directly to the two most outwardly located transducers; through the line $\mathbf{11}_1$ to the two adjacent transducers; through the line $\mathbf{11}_2$ to the transducers framing the central transducer; and, through the line $\mathbf{11}_3$, to the central transducer.

The same delay combination enables focusing on the reception, after which a switching means (not shown) activates a group of n transducers shifted from the first group to effect the scan.

Once the distance F has been determined, the distribution of delays to be adopted can be established by the application of conventional formulae.

For example, the delay Δt to be imposed on the energization of a transducer located at distance x from the center of the group of transducer elements for focusing at distance F must be, in the Fresnel approximation:

$$\Delta t=x^2/2F.C$$

where C is the speed of ultrasound in the propagation medium.

This variation can be simulated approximately with a small number of delays.

Similarly, it is possible to produce focusing on transmission or on reception by applying to the transducer elements $\mathbf{12}_i$, staggered delays according to a relationship which approximates to the theoretical relationship corresponding to a cylindrical distribution. FIG. 2 shows, in dashed lines, the theoretical delay distribution which would be produced between transducers as a function of their distance x from the center of the group for a parabolic relationship. The graph in a solid line shows the simulation of this parabolic relationship with sampling at several delay levels each separated by a constant interval τ. In the embodiment illustrated in FIG. 2 it is seen that the central transducer and the transducers of order 2, 3 and 4 on each side would receive the signal with a maximum delay, the transducers of order 5 and 6 would have to receive it with a delay diminished by τ, and so on.

Before passing on to the description of a particular circuit enabling the invention to be practiced, it should be stressed that the convex arrangement of the transducer elements shown in FIG. 1 leaves complete freedom as regards focusing in a plane perpendicular to the plane of scan. In the embodiment of the head shown in FIG. 3, this focus is ensured at a point N (which may be different on the focal point M in the other plane) by giving the generator of the piezoelectric ceramic 14 common to all transducers a concave shape. In particular, each metallized strip belonging to a transducer element may have a circular shape whose radius corresponds to the distance between the ceramic and the point N.

Another solution consists of placing, in front of the transducer elements, a lens, as illustrated in FIG. 4. In this case, the common ceramic may have the shape of a portion of a cylinder. The lens will be convex if the speed of the sound in its constituent material (for example, a hard synthetic elastomer) is less than the speed of sound in the tissues being monitored.

A circuit will now be described, with reference to FIG. 5, which permits electronic focusing at distance F, by means of a stepped delay on the transmission and on the reception of the type shown in FIG. 2, as well as scanning. This circuit is arranged to be associated with a system of N transducers $\mathbf{12}_1, \ldots, \mathbf{12}_i, \ldots, \mathbf{12}_N$, which can be pulse energized. The system provides, for each exploration shot, the energizing of n transducers $\mathbf{12}_i$, with a predetermined distribution of delays: for example, the system provides for application of the energizing signal with a maximum delay to the transducers of order 1, 2, 3 and 4. The system further provides a delay τ for the signal before application to the transducers of order 5 and 6, and so on.

The electronic system which will now be described enables the use of a number of transmission and reception multiplexers equal to n, hence which can be very widely different from the total number N of transducers. It is thus possible, for a given cost, to use multiplexers with a higher number of channels, sufficient to provide a high rate of sampling, hence high focusing accuracy, and lateral lobes of little importance.

The electronic system shown in FIG. 5 is designed to be associated with a probe comprising N transducer elements such as $\mathbf{12}_i$ each associated with a routing circuit 80.

The electronic system includes a first network of multiplexers 34. The number of multiplexers in that first network is not equal to the total number N of transducers of the linear array, but rather to the number n of transducers which are energized during a shot, so as to constitute an electronic lens. The number of transducers energized during the same shot may be as high as 40 when using a linear array of N=160 elements. In these circumstances, each "shot" will make use of a quarter of the total array. Each of the first multiplexers 34 is used in association with several transducers shifted by n. For example, the same multiplexer 34 will be associated with the transducers $12_i$, $12_{i+n}$, $12_{i+2n}$, $12_{i+3n}$ in the embodiment contemplated. This first network of multiplexers, which permits the selection of one of the a delay channels that is supplied by the transmission means, which comprise a pilot clock 38, a generator 39 and a register 15, is connected to the corresponding transducers through a second network of multiplexers, for effecting the addressing of the transducers. Each of these second multiplexers comprises a transmission element or transmitter unit 81 enabling a direct link to be established between the input-output access of the first corresponding multiplexer 34 and the circuit 80 of a transducer. It includes also a reception element or receiver unit 82 enabling the reception signal to transit in the other direction, towards the access of the associated multiplexer 34 through a preamplifier 33. The latter may be of particularly high quality, considering that its cost will have little influence on that of the whole device, since n preamplifiers will suffice for N transducers.

As for the circuits directly associated with the transducers, they can be of simple constitution. They may notably include a single component active on transmission, constituted, for example, by a V MOS transistor which has the advantage of very rapidly switching to a high power level, supplied by a voltage source −V, under the action of a control signal of low intensity coming from the second multiplexer.

The selection of the channel connected through the first multiplexer network to the transducers is effected from information supplied by shift registers 35 which, in the case where 16 channels are used, could be registers with four times four binary elements. Each of the registers 35 is applied to or associated with a first multiplexer 34 with a=16 channels; a second register is applied to each multiplexer, so that the set of switchings is effected by a number of elementary circuits 84 (shown within broken lines in FIG. 5) equal to n=40 only. It should be noted that switching from one group of n=40 transducers to the following group is done progressively by recycling of the information in the registers 35, as indicated by the line with several channels 85, and a recycler 86, constituted by a selector in FIG. 5.

By providing, for each register, four sets of four binary elements, it is possible to effect the scanning along a number of transmission and reception lines double the number of transducers, by providing the four following successive configurations:

1. A transmission lens configuration with an even number of transducers (40 for example).

2. A reception lens corresponding to the transmission lens with 40 transducers.

3. A transmission lens configuration shifted by a half transducer with respect to the preceding one, using an odd number of transducers (for example 39).

4. A reception lens configuration corresponding to the transmission configuration with an odd number of transducers.

The clock 87 controlling the registers 35 will produce a clock pulse before each transmission and a pulse after each transmission. An initiating system is provided so that the clock 87 produces a number of pulses sufficient to position the information, taken from memory means 37, in the n first registers 35. In this particular case, the first shot will be centered on the twentieth transducer of the bar. It is however possible to commence the exploration operation without waiting for the filling of the registers with the whole of the "lens".

The second multiplexer network is associated with a common control generator 88 which, for each shot, transmits a common command signal on line 89 which enables the unit 81 for a short period of time narrowly framing or encompassing the group of logic signals of the transmission command signal and the unit 82 during the corresponding time. The selection of the transducers supplied by the second multiplexer network is controlled by information supplied to two binary elements carried by shift registers 90 in cascade. This information for the two binary elements is produced for each frame by a counter 91 which divides the number of clock pulses by 40. The advance is ensured by a clock (not shown) which supplies one pulse per four clock pulses 87. The other basic circuits of the electronic system shown in block form in FIG. 5 can be relatively conventional and include a reception circuit 62 with delay correction (constituted, for example, by a delay line with multi-terminal connectors) and a processing circuit 25 for the signal fed to a display or storage system 57.

It is seen that the device according to the invention can be directly incorporated in any existing system with electronic focusing and scanning, at the cost of a simple modification of the variation in the delay or phase shift. The device uses a reduced number of different delays or phase shifts. Sector scanning is obtained quite naturally due to the form of the probe. The density difference of the scan lines between the surface zone and the deep zone of the organ to be explored is reduced, due to the fact that there is no convergence of a beam at the level of the point of entry into the organ. Contrary to what occurs in devices with electronic sector scanning by means of a bar of flat transducers as existed hitherto, the acoustic field produced by the device according to the invention does not depend on the angle of observation with respect to the middle plane. Finally, experience shows that the convex shape of the probe does not constitute any impediment to providing good contact with the skin.

I claim:

1. An electronic scanning ultrasonic echography device for exploration of an organ or other internal anatomical structure, said device comprising:

a probe having an external surface adapted for contact with a surface of a body to be examined and carrying a linear array of N identical transducer elements, where N is an integer, distributed at equal intervals along a part circular line having the convex side thereof facing toward said external surface of said probe, means for storing at least one distribution of time delays associated with n successive transducer elements, where n is a number less than N, corresponding to focusing at a predetermined distance from the center of said part circular line which is substantially larger than the radius of said part circular line, signal transmitting means and signal receiving means and switch means, cooperating with said storing means, for providing connection of a first group of n successive transducer elements to said signal transmitting means and signal receiving means with said distribution of time delays and thereafter providing connection of successive groups of n transducer elements at an increasing angular distance from said first group in accordance with a predetermined sequence. so as to provide sector scanning.

said signal transmitting means comprising a pulse generator. and means for delivering on a plurality of channels. from each said pulse of said pulse generator. a plurality of time pulses delayed by a predetermined time $\tau$ and by multiples of $\tau$, said switch means being arranged to control a plurality of amplifiers each associated with one of said transducers in response to a said pulse appearing on the channel associated with that amplifier. as selected by the storing means, and to direct the reflected signal from said one of said transducers to the associated channel, and said signal receiving means comprising a plurality of time delay elements, each connected to a particular one of said channels, for passing a signal received on that channel with the time delay associated with that channel.

2. A device according to claim 1, wherein the time delay elements comprise a plurality of delay lines.

3. In electronic scanning ultrasonic echography device. an electronic circuit arranged for cooperation with any of at least two probes each having an external surface for contact with a surface of a body to be examined and carrying a linear array of N identical transducer elements, where N is an integer, distributed at equal intervals along a line, the line of transducer elements of at least one of said probes being part circular with the convex side thereof being directed toward said external surface of the probe and having a radius of curvature different from the radius of curvature of the linear array of the other of said probes, said electronic circuit comprising:

a plurality of means each for storing a particular distribution of time delays relating to the radius of curvature of respective ones of said at least two probes and associated with n successive transducer elements said linear array, and switching means for selecting one of said storage means storing of a particular one of said distributions of time delays whereby a selected one of said at least two probes can be utilized, said circuit further comprising means and for connecting successive groups of n transducer elements at an increasing angular distance from said first group in accordance with a predetermined sequence so as to provide sector scanning.

4. A device for electronic scanning ultrasonic echographic exploration of an internal anatomical structure, said device comprising:

a probe having an external surface adapted for contact with a surface of a body to be examined and carrying a linear array of N identical transducer elements, where N is an integer, distributed at equal intervals along a line, a pulse generator for generating individual control pulses, means for storing at least one distribution of time delays selected among a plurality of predetermined time delays $\tau$, $2\tau$, . . . $(a-1)$ $\tau$, where a is a predetermined integer, and associated with n successive ones of said transducers, where n is an integer less than N, and corresponding to focusing at a predetermined distance from the center of said line, and switch means for temporarily connecting a group of n of said transducer elements to said generator so that said n transducer elements receive a said control pulse with said distribution of time delays and for shifting said group after each of said individual control pulses so as to provide scanning, said switch means comprising:

time delay means for delivering on different channels, from the same one of said individual control pulses, a plurality of respective energizing pulses separated by times $\tau$ or multiples of $\tau$, a first set of n multiplexers each for temporarily connecting one of said channels to an input-output terminal thereof, a second set of n multiplexers each having an input-output terminal connected to the input-output terminal of an associated one of said first set of multiplexers and multiplexing terminals connected to respective ones of said transducer elements which are spaced at intervals of n, each of said second set of multiplexers being arranged and controlled to connect one only of the associated transducer elements to the associated multiplexer of the first set for the time required for transmission of the energizing pulses corresponding to one control pulse and for reception an echo thereof.

5. A device according to claim 4, wherein each of the second multiplexers comprises a transmitter unit for providing a direct connection between said terminal of the associated first multiplexer and a transducer, and a a receiver unit for providing a connection through a preamplifier between the transducer and the terminal of the first multiplexer and wherein said transmitter and receiver units are controlled by means synchronized with the transmission means so as to block the transmitter unit during reception and to block the receiver unit during transmission.

6. A device according to claim 4, comprising a plurality of sets of second multiplexers each adapted for use with a particular one of a plurality of probes, the transducer elements of at least one of said probes being distributed along a convex part-circular line and said switch means including means for rendering operative one of said sets in accordance with the probe used.

* * * * *